US006764307B2

(12) United States Patent
Metrikin

(10) Patent No.: US 6,764,307 B2
(45) Date of Patent: Jul. 20, 2004

(54) POLYMER-METAL COMPOSITION RETAINER FOR SELF-LUBRICATING BEARING

(75) Inventor: Alex Metrikin, Los Angeles, CA (US)

(73) Assignee: Minebea Company, Ltd., Nagano-Ken (JP)

(*) Notice: Subject to any disclaimer, the term of this patent is extended or adjusted under 35 U.S.C. 154(b) by 0 days.

(21) Appl. No.: 09/819,334

(22) Filed: Mar. 28, 2001

(65) Prior Publication Data

US 2002/0142264 A1 Oct. 3, 2002

(51) Int. Cl.$^7$ .......................... A61C 1/05; F16C 33/44
(52) U.S. Cl. ................................ 433/132; 384/527
(58) Field of Search ........................ 433/131, 132; 384/523, 524, 525, 526, 527, 528, 529, 530, 531, 532, 533, 534, 572, 573, 574, 575, 576, 577, 580

(56) References Cited

U.S. PATENT DOCUMENTS

| | | | |
|---|---|---|---|
| 3,199,934 A | | 8/1965 | Van Wyk .................... 384/527 |
| 3,567,504 A | * | 3/1971 | Hopkins et al. ............ 384/276 |
| 3,632,368 A | | 1/1972 | Nelson ....................... 427/190 |
| 3,676,308 A | | 7/1972 | Brown |
| 3,843,962 A | | 10/1974 | Bogue ........................ 308/187 |
| 4,318,695 A | | 3/1982 | Lieb et al. .................. 433/132 |
| 4,414,241 A | | 11/1983 | Quella et al. |
| 4,488,977 A | | 12/1984 | Patrichi ...................... 508/103 |
| 4,508,396 A | | 4/1985 | Doi et al. .................... 384/463 |
| 4,966,552 A | | 10/1990 | Gonser ....................... 433/132 |
| 5,482,385 A | | 1/1996 | Yokota et al. .............. 384/572 |
| 5,516,214 A | | 5/1996 | Kakumoto et al. ......... 384/492 |
| 5,636,708 A | | 6/1997 | Wedeven et al. .......... 184/6.22 |
| 5,707,718 A | | 1/1998 | Matsukawa et al. |
| 5,752,773 A | | 5/1998 | Rosado et al. ............. 384/527 |
| 5,924,864 A | * | 7/1999 | Loge et al. ................. 433/131 |
| 5,988,891 A | * | 11/1999 | Yamamoto et al. ........ 384/463 |
| 6,007,251 A | | 12/1999 | Hayashida et al. ........ 384/492 |
| 6,113,278 A | * | 9/2000 | Ohira ......................... 384/527 |
| 6,431,761 B1 | * | 8/2002 | Yamaguchi et al. ....... 384/527 |

FOREIGN PATENT DOCUMENTS

| | | |
|---|---|---|
| EP | 0423313 B1 | 4/1991 |
| JP | 59074193 * | 4/1984 |

OTHER PUBLICATIONS

NHBB Precision Bearing Production (catalog) 1998 pp. 9–9 through 9–14; Other NHBB Products (catalog) 1998.
Miniature and Instrument Ball Bearings—Products and Engineering 1998; pp. 33, 38–40.
Ball Bearing Engineering (catalog) 1996, Subject Index, Materials, pp. 11–13, 15, 22 and 23.
We Know The Drill—Miniature & Instrument Bearings for Dental Applications (catalog) 2000.
New Materials boost bearing performance, Boylon, Mar. 11, 1999.
Translation of a Patent Journal Issued by the Japanese Patent Office entitled "A Bearing Device for Dental Hand Pieces". Inventor Kiyoshi Takimoto et al. Publication date Sep. 2, 1988.

* cited by examiner

*Primary Examiner*—John J. Wilson
(74) *Attorney, Agent, or Firm*—Schulte Roth & Zabel LLP; Joel E. Lutzker; Mayankkumar Dixit

(57) ABSTRACT

The retainer of the present invention is made of a composite material having a body made from a polymer, a layer of solid lubricant formed over the body by chemically coating the body with a porous layer of solid lubricant and impregnating the solid lubricant with another lubricant using conventional methods such as vacuum impregnation. The retainer is placed between an outer raceway and an inner raceway to form a self-lubricating bearing. The bearing made in this manner has high lubrication tolerance (i.e. it performs well in the absence of external lubrication). Because of its high lubrication tolerance, the bearing is suitable for use in various applications such as dental/medical hand pieces that are periodically sterilized and other applications which occasionally experience periods of lubrication starvation.

23 Claims, 2 Drawing Sheets

POLYMER-METAL COMPOSITION RETAINER FOR SELF-LUBRICATING BEARING

BACKGROUND OF THE INVENTION

1. Field of the Invention

This disclosure relates to a self-lubricating ball bearing which is suitable for use especially in a high-speed application such as in a dental handpiece.

2. Description of the Related Art

A conventional bearing includes an outer raceway, an inner raceway and a retainer (also known as a cage or a separator) with balls placed between the outer raceway and the inner raceway. The retainer separates and positions the balls at approximately equal intervals around the bearing's raceway. The retainer can be made from metallic or non-metallic materials. The non-metallic retainers are light weight, quiet, wear resistant and serve as an oil reservoir because of the material's porous structure. Non-metallic retainers are particularly suitable for use in high-speed ball bearings.

U.S. Pat. No. 3,199,934 describes a conventional self-lubricating bearing having an outer raceway, an inner raceway and a metallic retainer. The retainer of the patent is formed of a composition containing silver, platinum, molybdenum disulfides, lead oxide and silicon dioxide such that the composition material itself acts as a solid lubricant.

U.S. Pat. No. 3,863,962 teaches a retainer made from polymeric material having a filler, such as a metallic sulfide, that has desirable lubricating properties. U.S. Pat. No. 5,988,891 teaches a retainer made from a melt-moldable fluororesin used with a raceway having an adhered to film of solid lubricant. U.S. Pat. No. 4,966,552 teaches the use of ceramic balls to reduce friction between the balls and other parts of the bearing. Conventional non-metallic retainers can be made from a polymer or phenolic material. The conventional polymer retainers can be made from, for example, polyamide, polyamideimides, polyetherethrketones, Vespel™ or Meldin™. However such retainers have limited grease and oil retaining properties due to insufficient porosity. On the other hand, conventional phenolic retainers have better porosity and therefore better lubrication retaining properties, but are not as strong mechanically as polymer retainers and break, for instance, upon being subjected to repetitive autoclave cycles.

SUMMARY

None of the above mentioned patents teach the use of a solid lubricant in combination with another lubricant impregnated within the solid lubricant. Additionally, it is desirable to create a lubrication tolerant retainer with good mechanical properties for use in a ball bearing. It is also desirable to create a composite retainer from a strong polymer but with better lubrication retaining properties. Further, it is desirable to create a retainer which has a highly porous layer of solid lubricant capable of being impregnated with an additional lubricant.

The retainer of the present invention overcomes the aforesaid shortcomings of the prior art, while at the same time providing a wear resistant, mechanically strong retainer with a highly porous surface that is suitable for making lubrication tolerant bearings for use in dental handpieces and rotary tools.

The retainer of the present invention is made of a composite material having a body (or core) made from a polymer, and a layer of solid lubricant formed over the body by chemically coating the body with a porous layer of solid lubricant and impregnating the solid lubricant with another lubricant using a conventional method such as vacuum impregnation. The retainer is placed between an outer raceway and an inner raceway to form a self-lubricating bearing. The bearing made in this manner has high lubrication tolerance (i.e. it performs well in the absence of external lubrication). Because of its high lubrication tolerance, such a bearing is suitable for use in various applications such as dental/medical handpieces that are periodically sterilized, machine tool spindle motor applications which occasionally experience periods of lubrication starvation (such as at machine start-up), fan motors, DC motors, and stepping motors. It is also especially useful for any motor used in an environment hostile to a lubricant such as a vacuum environment or a high frequency occultation application in which lubricant is pushed off of the raceway surfaces by high frequency oscillation or high speed rotation.

Further features and advantages will appear more clearly on a reading of the detailed description, which is given below by way of example only and with reference to the accompanying drawings.

DETAILED DESCRIPTION

Figure 1:
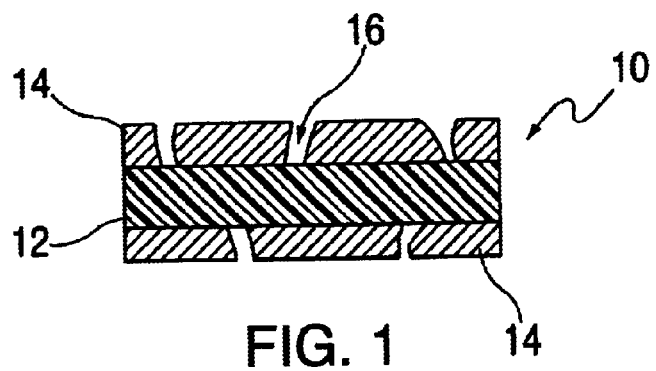
FIG. 1 is a cross-sectional view of a composite material.

FIG. 1 shows a cross-sectional view of a composite material 10. Composite material 10 includes a body 12 made from, for example, polyamideimide polymer. Body 12 may also be made from other materials suitable for making ball bearing retainers. For example, polyimides, polyetherethrketones, Vespel™ or Meldin™ may be used to make body 12. A layer 14 of solid lubricant is formed over body 12 by chemically coating body 12 with layer 14 made of a solid lubricant such as silver. Other solid lubricants (i.e. ductile platable metals) including gold and other chemi-platable precious metals can be used to form layer 14. Layer 14 formed from solid lubricant silver exhibits high porosity, and can have up to sixty percent volume porosity. Layer 14 may be formed using a conventional chemi-plating process, and the thickness of layer 14 may be one thousandth of an inch or that which is sufficient for adequate retention of a lubricant 16. In one embodiment the thickness of layer 14 is in the range of 3 ten thousandths to 5 ten thousandths of an inch. Due to the higher porosity provided by the chemi-plating process, lubricant retention by layer 14 is superior to a similar layer provided by conventional methods like electroplating. Porous layer 14 is impregnated with lubricant 16 using a conventional method such as vacuum impregnation, dipping in a dip tank or supplying the lubricant using a syringe. An example of lubricant 16 is grease. Other conventional lubricants such as oil may also be used to impregnate the layer.

Figure 2:
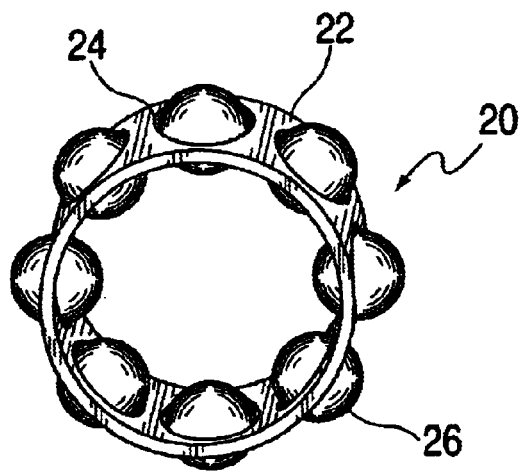
FIG. 2 is a perspective view of a retainer whose walls have the cross-section shown in FIG. 1.

FIG. 2 shows a retainer that has walls with cross-section similar to that illustrated in FIG. 1 and described previously.

Retainer 20 consists of a ring 22 with holes 24 formed through the wall of ring 22. Holes 24 are sized to receive a ball 26. Retainer 20 is made by plating body 12 (see FIG. 1) made from polyamideimide polymer with layer 14 of solid lubricant silver and impregnating porous layer 14 with lubricant 16 which in one embodiment is grease.

Figure 3:
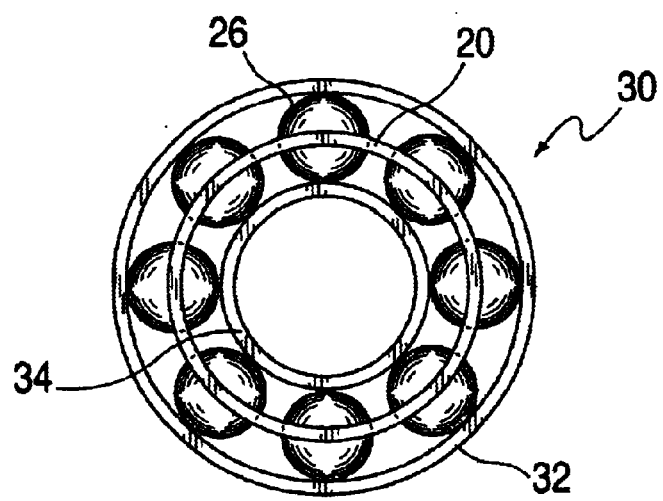
FIG. 3 is a plan view of a ball bearing made using the retainer of FIG. 2.

FIG. 3 shows a self-lubricating bearing 30 having an outer raceway 32 and an inner, raceway 34. Retainer 20 is placed between raceway 32 and raceway 34 to form self-lubricating bearing 30. Bearing 30 is capable of rotating at high speeds, for example, 500,000 revolutions per minute or higher. Bearing 30 has high lubrication tolerance (i.e. it performs well in the absence of external lubrication). Bearing 30 derives its high lubrication tolerance in part due to the better retention of lubricant 16 in porous layer 14 (see FIG. 1). Additionally, layer 14 which is formed from solid lubricant silver also contributes to making bearing 30 lubrication tolerant. In one embodiment further lubrication tolerance is obtained by using balls 26 that are made from ceramic. A detailed description of the ceramic used for making balls 26 is disclosed in U.S. Pat. No. 4,960,552. Because of high lubrication tolerance, bearing 30 is suitable for use in various applications such as dental/medical handpieces that are periodically sterilized, machine tool spindle motor applications which occasionally experience periods of lubrication starvation (such as at machine start-up), fan motors, DC motors, and stepping motors. It is also especially useful for any motor used in an environment hostile to a lubricant such as a vacuum environment or a high frequency occultation application in which lubricant is pushed off of the raceway surfaces by high frequency oscillation or high speed rotation.

Figure 4:
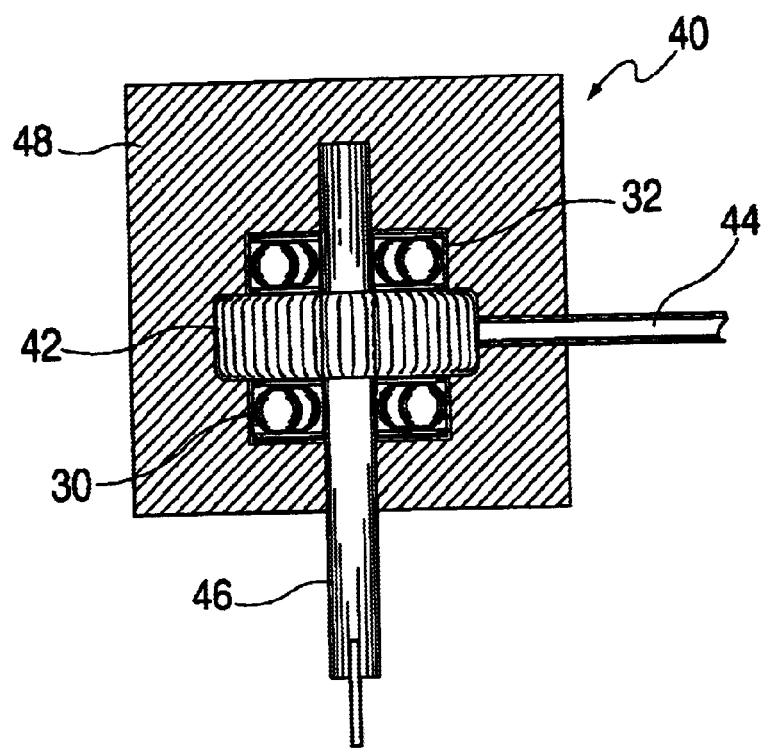
FIG. 4 is a cross-sectional view of a dental handpiece made using the bearing of FIG. 3.

FIG. 4 shows a portion of dental handpiece 40 having a turbine 42 driven by pressurized air supplied via air inlet 44. Turbine 42 is mounted on a shaft 46 and the entire assembly rotates in bearings 30 mounted on shaft 46 on two sides of turbine 42. The outer raceway 32 of each bearing 30 is captured in body 48 of handpiece 40. Bearings 30 use retainers 20 (see FIG. 2) which combine lubricant retaining properties of porous silver and solid lubricating capabilities of metallic silver with the strength and ability to withstand repetitive autoclave cycles of polyamideimide polymer. Therefore, a handpiece 40 using bearings 30 lasts longer and provides quiet operation at speeds of 500,000 revolutions per minute or higher even after undergoing numerous autoclave cycles.

Figure 5:
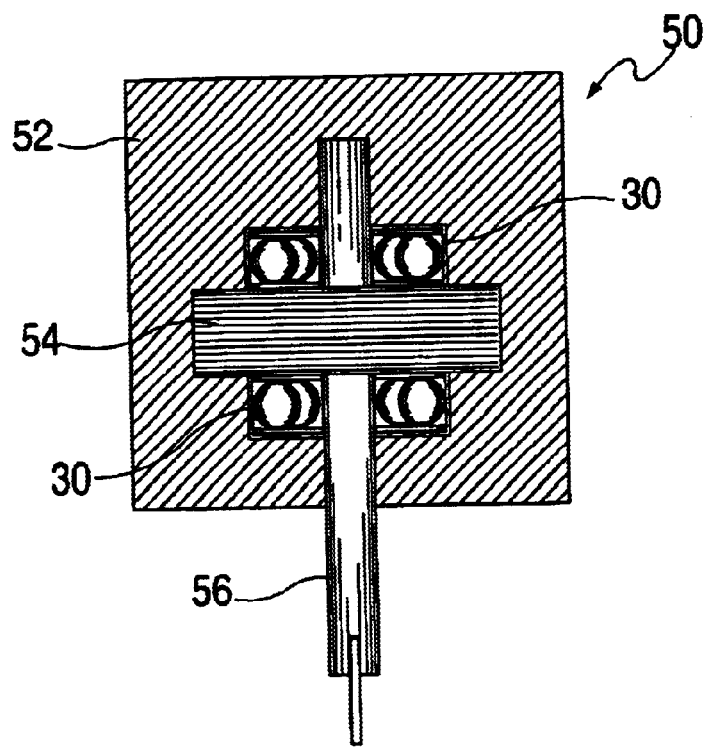
FIG. 5 is a cross-sectional view of a motor made using the bearing of FIG. 3.

FIG. 5 shows a motor 50 having housing 52 and an armature 54. Armature 54 is mounted on a shaft 56 that rotates in bearings 30 mounted on shaft 56 on two sides of armature 54. The outer raceway 32 of each bearing 30 is captured in housing 52 of motor 50. Use of bearings 30, as described previously in reference to handpiece 40 (see FIG. 4), provides longer useful life with quiet operation at speeds of 500,000 revolutions per minute or more even in the absence of periodic lubrication of the bearings.

While a preferred embodiment of the invention has been described, various modifications will be apparent to one skilled in the art in light of this disclosure and are intended to fall within the scope of the appended claims. For example, the bearings of the invention may be used in any type of motor or motor design. The balls and/or raceways may be made of similar materials and construction to that described with respect to the retainer, or just one raceway may be made of such material and construction for any application in a tool or motor. The retainer may be of any known design in addition to the ring with holes disclosed in FIG. 2. The retainer may be a two or plural piece retainer or cage and only one or more pieces may be made of the materials and construction described herein.

I claim:

1. A bearing retainer comprising:
    a core consisting of a polymer;
    a first layer of pure solid lubricant chemically adhered to said core, said first layer being porous and having antibacterial properties and suitable for use in biological environments; and
    a second lubricant impregnated in the pores of said first layer.

2. The bearing retainer of claim 1, wherein said core is made from a material selected from a group consisting of polyimides, polyamideimides and polyetherethrketones.

3. The bearing retainer of claim 1, wherein said first layer is made from a ductile platable solid lubricant.

4. The bearing retainer of claim 1, wherein said first layer is made from a material selected from a group consisting of silver, and gold.

5. The bearing retainer of claim 1, wherein said second lubricant is selected from a group consisting of oil and grease.

6. The bearing retainer of claim 1, wherein the thickness of said first layer is in the range of 3 to 5 ten thousandths of an inch.

7. The bearing retainer of claim 1, wherein volume porosity of said first layer is in the range of five to sixty percent.

8. A rotary tool having the bearing retainer of claim 1 comprising:
    a rotating element;
    a drive for driving said rotating element; and
    at least one bearing for rotatably mounting said drive, said bearing including the retainer of claim 1.

9. The rotary tool of claim 8, wherein the drive is an air turbine for a dental handpiece.

10. The rotary tool of claim 8, wherein the drive is a motor for driving a spindle.

11. The rotary tool of claim 8, wherein said core is made from a material selected from a group consisting of polyimides, polyamideimides and polyetherethrketones.

12. The rotary tool of claim 8, wherein said first layer is made from a ductile platable solid lubricant.

13. The rotary tool of claim 8, wherein said first layer is made from a material selected from a group consisting of silver, and gold.

14. The rotary tool of claim 8, wherein said second lubricant is selected from a group consisting of oil and grease.

15. The rotary tool of claim 8, wherein the thickness of said first layer is in the range of 3 to 5 ten thousandths of an inch.

16. The rotary tool of claim 8, wherein the volume porosity of said first layer is in the range of five to sixty percent.

17. A ball bearing comprising:
    an outer raceway;
    an inner raceway;
    balls;
    a retainer, said retainer being made from a composite material having
        a core consisting of a polymer;
        a first layer of pure solid lubricant chemically adhered to said core, said first layer being porous and having antibacterial properties and suitable for use in biological environments; and a second lubricant impregnated in the pores of said first layer, wherein said retainer housing said balls is placed between said outer raceway and said inner raceway.

18. The ball bearing of claim 17, wherein said core is made from a material selected from a group consisting of polyimides, polyamideimides and polyetherethrketones.

19. The ball bearing of claim 17, wherein said first layer is made from a ductile platable solid lubricant.

20. The ball bearing of claim 17, wherein said first layer is made from a material selected from a group consisting of silver, and gold.

21. The ball bearing of claim 17, wherein said second lubricant is selected from a group consisting of oil and grease.

22. The ball bearing of claim 17, wherein the thickness of said first layer is in the range of 3 to 5 ten thousandths of an inch.

23. The ball bearing of claim 17, wherein the volume porosity of said first layer is in the range of five to sixty percent.

* * * * *